United States Patent
Colman et al.

[11] Patent Number: 6,057,475
[45] Date of Patent: May 2, 2000

[54] PROCESS FOR THE PRODUCTION OF ACETIC ACID

[75] Inventors: Derek Alan Colman, Hants; Jeremy Bernard Cooper, East Sussex; Andrew Richard Lucy, East Riding of Yorkshire, all of United Kingdom

[73] Assignee: BP Chemicals, Limited, London, United Kingdom

[21] Appl. No.: 09/357,371

[22] Filed: Jul. 20, 1999

Related U.S. Application Data

[63] Continuation of application No. PCT/GB98/00168, Jan. 20, 1998.

[30]     Foreign Application Priority Data

Jan. 22, 1997 [GB] United Kingdom ............... 9701251

[51] Int. Cl.[7] .................................................. C07C 51/21
[52] U.S. Cl. ............................................................. 562/549
[58] Field of Search ............................................. 560/549

[56]                 References Cited

U.S. PATENT DOCUMENTS

| | | |
|---|---|---|
| 3,644,512 | 2/1972 | Onopchenko et al. . |
| 3,923,882 | 12/1975 | Kiff . |
| 4,032,570 | 6/1977 | Schulz et al. . |
| 4,111,986 | 9/1978 | Zimmerschied . |
| 4,158,740 | 6/1979 | Lese et al. . |
| 4,900,480 | 2/1990 | Litz et al. . |
| 5,371,282 | 12/1994 | Kingsley et al. . |

FOREIGN PATENT DOCUMENTS

| | | |
|---|---|---|
| 0 018 729 A1 | 11/1980 | European Pat. Off. . |
| 0 126 488 | 11/1984 | European Pat. Off. . |
| 721 914 | 1/1955 | United Kingdom . |
| 1 020 797 | 2/1966 | United Kingdom . |
| 1 197 790 | 8/1970 | United Kingdom . |
| 1 266 678 | 3/1972 | United Kingdom . |
| 1 528 771 | 10/1978 | United Kingdom . |
| 1 531 247 | 11/1978 | United Kingdom . |
| 2 072 667 | 10/1981 | United Kingdom . |

OTHER PUBLICATIONS

Roby et al, "Oxide safely with pure oxygen," Chemtech, pp. 39–46 (1996).

Process Review: Polyester, ECN Chemscope, pp. 16–17.Jun. 1996.

Rouchaud et al, Competitive Liquid–Phase Oxidation of Butanes, I&EC Process Design and Development, vol. 7, No. 2, pp. 295–300 (1968).

*Primary Examiner*—Gary Geist
*Assistant Examiner*—Robert W. Deemie
*Attorney, Agent, or Firm*—Nixon & Vanderhye

[57]                    ABSTRACT

Process for the liquid phase oxidation of butane to produce acetic acid in which oxygen and butane are reacted in the presence of a cobalt catalyst in a liquid reaction composition in an oxidation reaction zone at a temperature in the reaction zone in the range of 136° to 150° C., while continuously maintaining a concentration of oxygen throughout the reaction zone equivalent to a partial pressure of oxygen greater than two bar. The concentration of cobalt oxidation catalyst in the liquid reaction composition is at least 0.12% by weight cobalt and up to its limit of solubility in the liquid reaction composition.

5 Claims, 8 Drawing Sheets

Reaction rate and % oxygen in overhead gas phase versus time.

FIG. 3 Repeated injections of three barg oxygen.

FIG. 4a 3% Catalyst at 7 bar oxygen.

FIG. 4b Oxygen consumption versus time.

FIG. 5  1% Catalyst, 10 bar oxygen, high temperature.

FIG. 6

PROCESS FOR THE PRODUCTION OF ACETIC ACID

This Application is a con of PCT/G898/00168 filed Jan. 20, 1998.

This invention relates to the production of acetic acid by the oxidation of butane using a cobalt catalyst.

The cobalt-catalysed oxidation of butane to produce acetic acid is a known process, and is described for example in U.S. Pat. No. 4,032,570, U.S. Pat. No. 4,158,740, GB 2072667, EP-A-0018729, U.S. Pat. No. 3,923,882 and GB 1531247.

U.S. Pat. No. 4,032,570 relates to a process for converting butane to a product predominating in acetic acid by contacting butane with molecular oxygen-containing gas in the presence of a soluble cobalt compound at a concentration of 0.5 to about 20% by weight cobalt based upon the lower fatty acid in the reaction composition at a temperature of about 200° to about 250° F. ( about 93 to about 121° C.). The partial pressure of oxygen is not stated. Whilst U.S. Pat. No. 4,032,570 states at col. 3 lines 5 to 9 that the reaction temperature can be from about 150° to about 275° F. ( about 65 to about 135° C.), and most preferably from about 200° to about 250° F. ( about 93 to about 121° C.), all the examples except one were performed at a temperature no greater than 115° C. The process of U.S. Pat. No. 4,032,570 may thus be characterised as operating generally at a low reaction temperature. The experiment performed at 131° C. (Run 5 in table 1) apparently shows a lower yield of butane converted to total product than, for example, at the lower temperature of Run 4.

U.S. Pat. No. 4,158,740 relates to a process for converting butane to acetic acid in the presence of cobaltic ions at elevated temperature in the range of about 75° to about 130° C. and elevated pressure in the range of about 200 to 500 psi absolute (about 14 to 35 kilograms per square centimeter) whilst maintaining a partial pressure of molecular oxygen of about 0.6 to about 15 psi ( about 0.04 to about 1.1 kilograms per square centimeter). According to U.S. Pat. No. 4,158,740, it is critical that the partial pressure of molecular oxygen be maintained in this specified range to obtain extremely high conversions of butane and extremely high yields of acetic acid. Whilst U.S. Pat. No. 4,158,740 states the elevated temperature to be about 75° to about 130° C., the preferred range is stated to be about 90° C. to about 120° C. and examples of operation only at 110° C. are given. The process of U.S. Pat. No. 4,158,740 may be characterised as operating at low partial pressure of oxygen and generally a low reaction temperature.

According to GB 2072667, butane may be oxidised to acetic acid by oxygen at a total pressure of 200–1000 psig, in acetic acid solvent, at a temperature between 80–150° C., in the presence of a cobalt acetate concentration of at least 0.1%, but no more than 3%, based on the weight of the reaction mixture and an iron concentration of below 1000 parts per million in the catalyst recycle stream and a succinic acid by-product concentration below saturation in the reaction media. Whilst it is stated that a small amount of oxygen is desirable in the reactor effluent and oxygen concentration at the analyser should be 0.1 to 10%, preferably 1 to 8% the partial pressure of oxygen is not explicitly stated in the examples. Although, in control B, oxygen concentration at the analyser was stated to be at least 2.0% which is estimated to be at least 0.7 bar.

EP-A-001 8729 relates to a cobalt catalysed, liquid phase oxidation of $C_3$ to $C_7$ aliphatic hydrocarbons at a temperature of 70 to 150° C. and a catalyst concentration of 0.1 to 10% by weight cobalt. The partial pressure of oxygen in the examples is not given but can be estimated to be about 2 bar or less.

It has now been unexpectedly found that using a package of operating conditions, namely temperature in the range 120 to 180° C. and high oxygen partial pressures, increasing cobalt catalyst concentration increases the rate of butane oxidation.

Thus according to the present invention there is provided a process for the liquid phase oxidation of butane to produce acetic acid by reacting oxygen and butane in the presence of a cobalt catalyst in a liquid reaction composition in an oxidation reaction zone characterised in that the process is performed at a temperature in the reaction zone in the range 120° to 180° C., whilst continuously maintaining a concentration of oxygen throughout the reaction zone equivalent to a partial pressure of oxygen greater than 2 bar, and a concentration of cobalt oxidation catalyst in the liquid reaction composition of at least 0.12% by weight cobalt and up to its limit of solubility in the liquid reaction composition.

The process of the present invention operates at a temperature in the range 120° to 180° C. whilst continuously maintaining a high partial pressure of oxygen throughout the reaction zone and a high cobalt catalyst concentration to obtain a high reaction rate.

Oxygen may be fed to the reaction zone on its own and/or in a mixture, for example, with air, recycled gases and/or inert gases such as nitrogen and carbon dioxide. Butane may be fed to the reaction zone, preferably as n-butane, although an n-butane/isobutane mixture may be used. Typically, greater than 95% of the butane feed is n-butane. Cobalt oxidation catalyst may be introduced to the reaction zone as a solid, or dissolved in a suitable solvent, for example, acetic acid. A suitable solvent, preferably acetic acid, is also present in the reaction zone. These components may be fed to the reaction zone as recycle components.

The liquid reaction composition may comprise (i) cobalt oxidation catalyst, up to its limit of solubility in the reaction composition, for example up to about 1.2% by weight cobalt, (ii) acetic acid, for example about 35% by weight, (iii) water, for example about 6% by weight, (iv) butane, for example about 40% by weight, and (v) dissolved oxygen. Other compounds such as intermediates and/or by-products may also be present in the liquid reaction composition for example, esters, ketones and carboxylic acids.

Preferably, materials which have an adverse effect on the oxidation reaction, such as certain metals, for example chromium, and certain non-metals, for example sulphur, are kept to a minimum in the reaction composition, for example by suitable selection of materials of construction of the reactor and associated vessels and pipework and/or by the use of removal processes such as ion exchange resin beds.

The total pressure in the reaction zone is preferably greater than 35 barg.

The temperature in the reaction zone is maintained in the range 120° to 180° C., preferably in the range 135° to 180° C., more preferably in the range 136° to 150° C., especially 140 ≧ 150° C. A constant temperature may be maintained in the reaction zone, for example, by passing a process stream from the reaction zone through an external cooling means and returning it to the reaction zone.

Preferably, bubbles of gas comprising oxygen and gaseous products are maintained essentially in dispersed form in the liquid reaction composition and there is no gas/liquid interface with an overhead gas phase. Thus, the reaction zone is maintained full of recirculating liquid reaction composition and dispersed gas bubbles. This ensures that the only gas phase present is that in the bubbles. Various methods may be employed to enhance the recirculation of the liquid reaction composition, for example, jet mixing using an oxygen-containing gas and/or a recirculated liquid stream. Since the contents of the reaction zone are fully mixed, the partial pressure of oxygen throughout the reaction zone (that pressure which would be formed if a vapour space were in equilibrium with the liquid contents) is constant. A high partial pressure of oxygen may be maintained throughout the reaction zone without the safety consequences of a flammable mixture because there is no overhead gas phase. Such a partial pressure is at least 2 bar and preferably at least 4 bar. Preferably the partial pressure is up to 20 bar. A typical oxygen partial pressure is about 9 bar.

Methods of introducing gas into a liquid without the formation of a gas/liquid interface are described in U.S. Pat. No. 4,900,480, U.S. Pat. No. 5,371,283, CHEMTECH February 1996, pages 39 to 46, and ECN Chemscope, June 1996, pages 16–17. These do not describe a process for the cobalt-catalysed oxidation of butane to produce acetic acid, as in the present invention.

Thus according to one embodiment of the present invention there is provided a process for the production of acetic acid which comprises:

(a) reacting oxygen and butane at a temperature in the range 120° to 180° C., in a recirculating first liquid reaction composition in a first reaction zone to produce acetic acid, the first liquid reaction composition comprising cobalt oxidation catalyst, butane, dissolved oxygen, acetic acid and water, and having no gas/liquid interface with an overhead gas phase, whilst continuously maintaining oxygen dispersed in the liquid and maintaining a concentration of oxygen in the liquid throughout the first reaction zone equivalent to a partial pressure of oxygen greater than 2 bar, and a concentration of cobalt oxidation catalyst in the first liquid reaction composition of at least 0.12% by weight cobalt and up to its limit of solubility in the first liquid reaction composition;

(b) withdrawing from the first reaction zone at least a portion of the first liquid reaction composition, together with entrained oxygen, and passing it to a bubble column reaction zone in which there is maintained a second liquid reaction composition comprising cobalt oxidation catalyst, butane, dissolved oxygen, acetic acid and water, and reacting the entrained and dissolved oxygen with butane in the second liquid reaction composition in the bubble column reaction zone to produce further acetic acid; said second liquid reaction composition being in contact with an overhead gas phase comprising oxygen at a concentration less than the lower flammability limit of the oxygen therein;

(c) withdrawing at least a portion of the second liquid reaction composition from the bubble column reaction zone, recovering acetic acid and optionally other co-products therefrom and recycling to the first reaction zone cobalt oxidation catalyst from the withdrawn composition; and (d) withdrawing overhead gas phase from the bubble column reaction zone, separating unreacted butane reactant therefrom and recycling it to the first reaction zone.

This embodiment of the present invention provides a process for the oxidation of butane to acetic acid which both enables high partial pressures of oxygen to be used without the safety consequences of a flammable overhead gas phase and to achieve complete mixing of gas and liquid. This is achieved through use of a reactor specifically designed for this purpose. Thus according to a further aspect of the present invention there is provided a reactor for use in the production of acetic acid comprising two reaction zones wherein a first reaction zone is capable of accommodating a recirculating first liquid reaction composition with no gas/liquid interface with an overhead gas phase and a second reaction zone capable of accommodating a second liquid reaction composition with a gas/liquid interface with an overhead gas phase and said first reaction zone adapted to accommodate an inlet means for gas and/or liquid and a baffle means adapted in use to disperse throughout the first reaction zone gas and/or liquid introduced through the inlet means.

Unlike conventional reactors which have either a stirrer or entrain gas from a head space using a liquid jet, the reactor of the present invention provides efficient dispersion of the gas by introducing the gas through the nozzle with the recirculating flow into a jet which is dissipated radially in the reactor by a baffle. This radial dissipation of the jet generates liquid mixing regions into which the gas bubbles are entrained. Consequently, the first reaction zone does not have a head space which is of course undesirable with the reactants of the present process. A further advantage with the reactor of the present invention is due to the radial dissipation of the liquid jet and gas, local concentration of gas is kept to a minimum, there is less coalescence and the gas bubbles will remain in the liquid for a longer period of time. Without the baffle gas bubbles coalesce and exit the reactor more readily.

The first reaction zone comprises an inlet means and a baffle means. Suitably, the first reaction zone has a height to diameter ratio of 1 and a vertical axis. The inlet means may suitably be an orifice nozzle, a straight sided nozzle or the like. It is preferred that the nozzle is an orifice nozzle. The nozzle may be directed vertically downwards into the reaction zone. Whilst the position of the nozzle is not crucial to the process, it is preferred that the nozzle be approximately one third of the height from the top of the reaction zone. It will of course be understood that this height may vary with differing reactor geometries.

As regards the baffle means, this may be a disc or plate or the like. The baffle should be positioned with respect to the nozzle inlet to ensure that the gas/liquid stream is diverted radially within the reactor. Where the baffle means is a plate, the plate is suitably positioned perpendicular to the direction of the gas/liquid stream exiting the inlet means. Thus, if the inlet nozzle, is directed vertically downwards in the reactor, the baffle means will be positioned horizontally or substantially horizontally. As regards height, it is preferred to position the baffle one third of the way up the reactor from the base.

The first reaction zone also contains a recirculating first liquid reaction composition with no gas/liquid interface with an overhead gas phase. This allows for high partial pressures of oxygen to be maintained in the first reaction zone without the safety consequences of a flammable overhead gas phase. The present work has shown that, for high partial pressures of oxygen, increasing the concentration of catalyst increases the reaction rate and this allows for an overall high production rate of acetic acid. The present work also shows that at high catalyst concentrations increasing the partial pressure of oxygen increases the reaction rate and this allows for an overall high production rate of acetic acid.

At least a portion of the first liquid reaction composition is passed to a bubble column reaction zone which is a bubble column reactor containing a second liquid reaction composition with a gas/liquid interface with an overhead gas phase having an oxygen concentration less than the lower flammability limit of the oxygen therein. As bubbles of entrained oxygen move through the bubble column reaction zone the oxygen concentration therein falls as oxygen reacts with butane in the second liquid reaction composition to produce further acetic acid thus consuming the oxygen, and carbon oxides pass from the reaction composition into the bubbles, so that the overhead gas phase has an oxygen concentration less than the lower flammability limit of the oxygen therein.

Oxygen may be fed to the first reaction zone on its own and/or in a mixture, for example, with air, recycled gases and/or inert gases such as nitrogen and carbon dioxide. Butane may be fed to the first reaction zone, preferably as n-butane, although an n-butane/isobutane mixture may be used. Typically, greater than 95% of the butane feed is n-butane. Cobalt oxidation catalyst may be introduced to the first reaction zone as a solid, or dissolved in a suitable solvent, for example, acetic acid. A suitable solvent, preferably acetic acid, is also present in the first reaction zone. These components may be recycled from the bubble column reaction zone.

The first liquid reaction composition comprises (i) cobalt oxidation catalyst, up to its limit of solubility in the reaction composition, for example up to about 1.2% by weight cobalt, (ii) acetic acid, for example about 35% by weight, (iii) water, for example about 6% by weight, (iv) butane, for example about 40% by weight, and (v) dissolved oxygen. Other compounds such as intermediates and/or by-products may also be present in the liquid reaction composition for example, esters, ketones and carboxylic acids.

Preferably, materials which have an adverse effect on the oxidation reaction, such as certain metals, for example chromium, and certain non-metals, for example sulphur, are kept to a minimum in the reaction composition, for example by suitable selection of materials of construction of the reactor and associated vessels and pipework and/or by the use of removal processes such as ion exchange resin beds.

Bubbles of gas in the first liquid reaction composition are maintained essentially in dispersed form in the recirculating first liquid reaction composition and there is no gas/liquid interface with an overhead gas phase. A high partial pressure of oxygen may be maintained in the first reaction zone without the safety consequences of a flammable mixture because there is no overhead gas phase. Such a partial pressure is at least 2 bar and preferably at least 4 bar. Preferably the partial pressure is up to 20 bar. A typical oxygen partial pressure is about 9 bar. The total pressure of the first reaction zone is preferably greater than 35 barg.

The temperature in the first reaction zone is maintained in the range 120° to 180° C., preferably in the range 135° to 180° C., more preferably in the range 135° to 150° C., especially in the range 140–150° C. A constant temperature may be maintained in the first reaction zone, for example, by passing a process stream from the first reaction zone through an external cooling means and returning it to the reaction zone.

The first reaction zone is separated from the bubble column reaction zone by a means which allows at least a portion of the first liquid reaction composition together with entrained oxygen to pass to the bubble column reaction zone without the formation of a gas/liquid interface in the first reaction zone. This separation means may be effected, for example, by arranging the first and second reaction zones one above the other in a reactor, the zones being separated by baffles or by a narrowing of the reactor diameter.

Preferably, there is little, if any, recirculation of the gas or liquid in the bubble column reaction zone and, because of this, the second liquid reaction composition varies along the length of the bubble column reaction zone. Typically, the second liquid reaction composition withdrawn from the top of the bubble column reaction zone comprises; (i) cobalt oxidation catalyst, up to its limit of solubility in the reaction composition, for example up to about 1.2% by weight cobalt, (ii) acetic acid, for example about 62% by weight, (iii) water, for example about 11% by weight, (iv) butane, for example about 10% by weight and (v) small amounts of dissolved oxygen. Other compounds such as intermediate and/or by-products may also be present in the second liquid reaction composition, for example, esters, ketones and carboxylic acids.

Reaction of oxygen and butane continues in the bubble column reaction zone (suitably, at least 5% of the overall oxygen consumption and typically, about one sixth of the overall oxygen consumption occurs in the bubble column reaction zone). The bubble column reaction zone is distinguished from the first reaction zone in that there is little, if any, recirculation of gas or reaction composition and it has a gas/liquid interface with an overhead gas phase. Some recirculation of the liquid composition may occur in the bubble column reaction zone but it should be kept as low as possible. Entrained and dissolved oxygen introduced into the bubble column reaction zone is consumed by further reaction so that the oxygen concentration in the overhead gas phase of the bubble column reaction zone is less than the lower flammable limit of oxygen therein.

Oxygen in the overhead gas phase may also be reduced by the use of an inert purge gas, for example, carbon dioxide or nitrogen, and/or by the vaporisation of butane. The latter method has the advantage of not necessarily requiring a purge gas.

In a preferred embodiment, the bubble column reaction zone is operated such that the temperature rises from (a) the point of introduction of the first liquid reaction composition and the entrained oxygen to (b) the overhead gas phase, preferably using the heat provided by the reaction itself, thus helping to consume oxygen and hence maintaining the oxygen concentration in the overhead gas phase less than the lower flammability limit of oxygen therein. A suitable temperature range for the bubble column reaction zone is in the range 120 to 200° C.

Suitably, the oxygen concentration in the overhead gas phase is maintained in the range less than 10% v/v, preferably less than 5% v/v. Suitably, the total pressure in the bubble column reaction zone is greater than 35 barg.

A portion of the second liquid reaction composition is withdrawn from the bubble column reaction zone, from which (a) acetic acid and optionally other products such as propionic acid and methyl ethyl ketone are recovered, and (b) cobalt oxidation catalyst is separated and recycled to the first reaction zone.

Overhead gas phase is withdrawn from the bubble column reaction zone from which butane is separated and recycled to the first reaction zone, for example by using a scrubber provided with a feed of a liquid recycle process stream.

The present invention is illustrated with reference to FIGS. 1 to 6 and the following experiments.

FIG. 4a is a graph of ballast pressure versus time and FIG. 4b is a graph of oxygen consumption rate versus time for the batch autoclave experiment of FIG. 4a.

Figure 1:
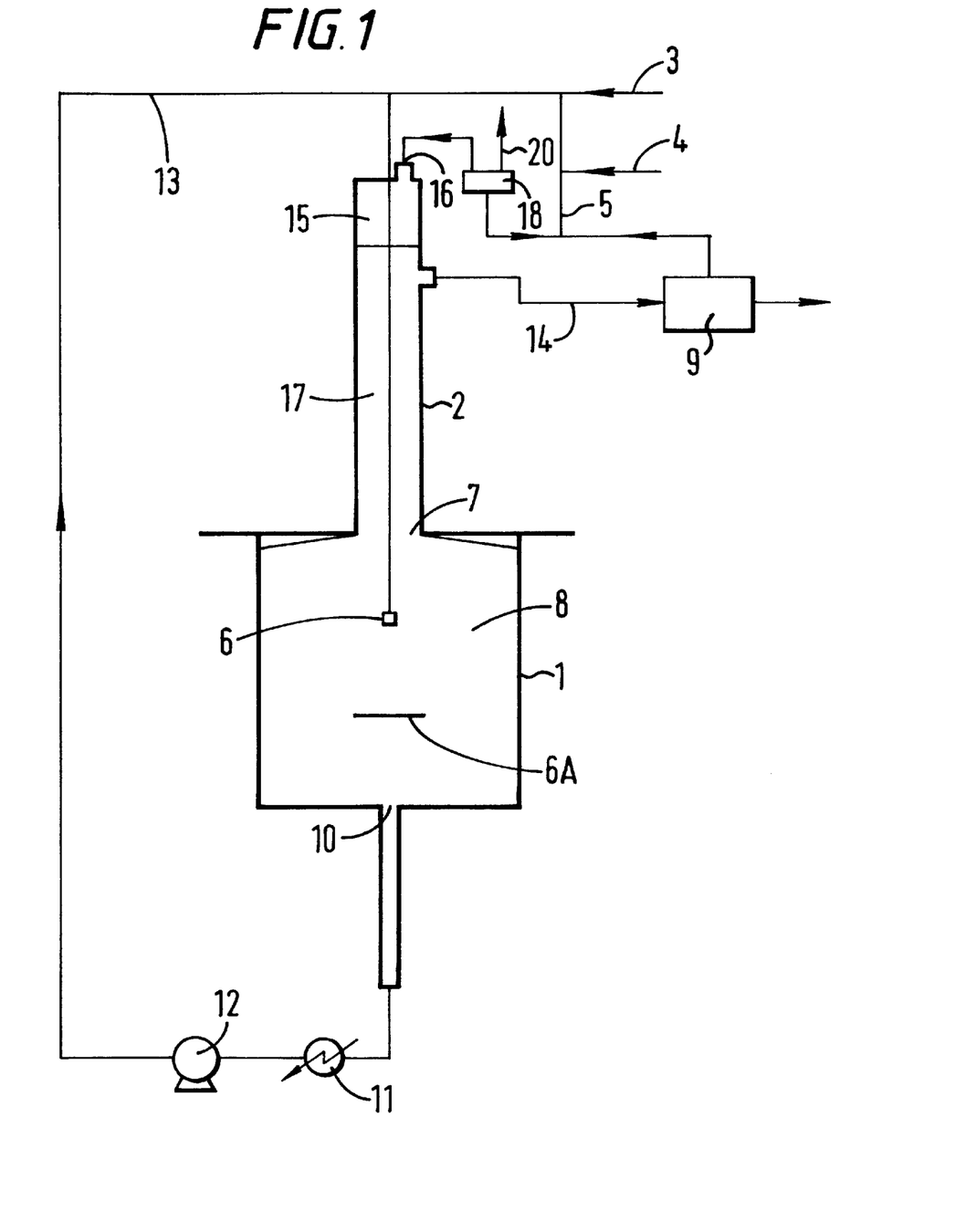
FIG. 1 represents in schematic form, a reactor for use in the present invention.

FIG. 1 represents in schematic form, a reactor for use in the present invention comprising two reaction zones, a first reaction zone (1) and a bubble column reaction zone (2). The first reaction zone has a supply inlet for oxygen (3), a supply inlet for butane (4) and supply means for liquid recycle components (5). One or more of these inlets may be combined to reduce the number of pipes to the reactor. The inlets are connected to a communal nozzle inlet (6). Gas/Liquid exiting the nozzle inlet (6) contacts the baffle means (6A) a plate (6A) positioned below the inlet (6). The first reaction zone is connected to the bubble column reaction zone by an opening (7) which allows, in use, a portion of the first liquid reaction composition (8) and entrained oxygen to be withdrawn from the first reaction zone and passed to the bubble column reaction zone without creating an overhead gas phase in the first reaction zone. The top of the first reaction zone is conical in order to avoid gas build up and direct gas bubbles leaving the zone towards the second zone. The first reaction zone is provided with an external recirculating means for the first liquid reaction composition which comprises an outlet (10), a cooler (11), a pump (12) and return line (13). The bubble column reaction zone has a liquid outlet (14) and an overhead gas phase outlet (16).

Figure 1A:
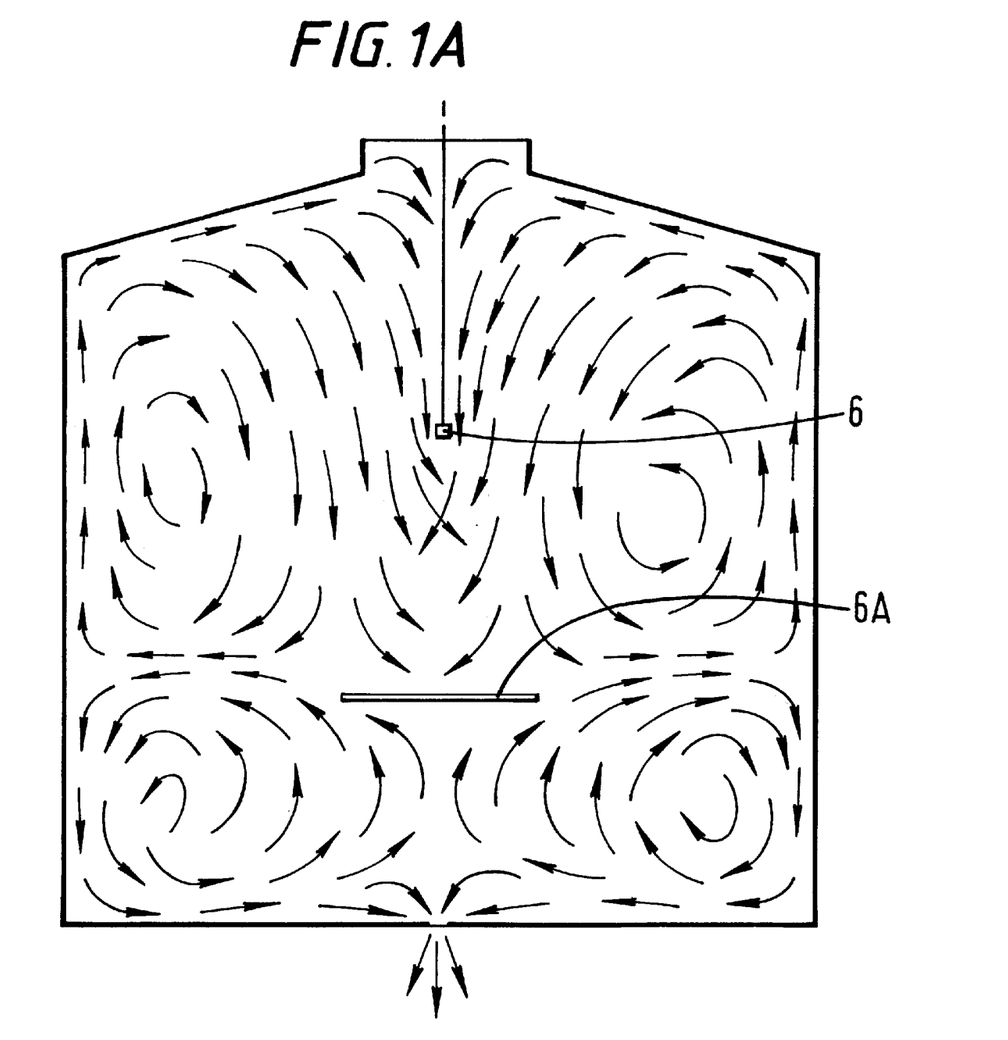
FIG. 1A represents the velocity vectors of the liquid phase in the first reaction zone.

FIG. 1A shows the liquid mixing pattern in the first reaction zone which is generated by the gas/liquid jet exiting the nozzle (6) and being radially directed by the baffle means (6A).

In use, oxygen, butane and liquid recycle components are introduced into the first reaction zone through inlets (3), (4) and (5) respectively and through return line (13). The oxygen and butane are reacted in the first liquid reaction composition is the first reaction zone to produce acetic acid. The first liquid reaction composition comprises cobalt oxidation catalyst, acetic acid, dissolved oxygen, butane and water and is maintained recirculating by the flow of components through communal nozzle inlet (6). The first reaction zone is maintained at a temperature in the range 120° to 180° C. and there is continuously maintained a concentration of oxygen throughout the first reaction zone equivalent to a partial pressure of oxygen greater than 2 bar and a concentration of cobalt oxidation catalyst in the first liquid reaction composition of at least 0.12% by weight cobalt and up to its limit of solubility. Part of the first liquid reaction composition (8) is withdrawn, together with entrained oxygen, from the first reaction zone and passed through opening (7) to the bubble column reaction zone. There is no gas/liquid interface with an overhead gas phase in the first reaction zone. The bubble column reaction zone has an overhead gas phase (15) and a second liquid reaction composition (17) which comprises butane, cobalt oxidation catalyst, acetic acid and water. Reaction continues as the entrained and dissolved oxygen moves up through the second liquid reaction composition (17) thus helping to maintain the oxygen concentration in the overhead gas phase (15) less than the lower flammable limit of oxygen therein. Vaporisation of butane also occurs in the bubble column reaction zone, this causes displacement of oxygen in the overhead gas phase thus also helping to maintain the oxygen concentration in the overhead gas phase less than the lower flammable limit of oxygen therein. Second liquid reaction composition is withdrawn from the bubble column reaction zone through outlet (14) and from this, acetic acid is recovered in recovery means (9) and a portion of the composition comprising cobalt oxidation catalyst is recycled to the first reaction zone through recycle means (5). Overhead gas phase is withdrawn from the bubble column reaction zone through outlet (16) and from this butane is separated by separation means (18) and is recycled to the first reaction zone through line (5) together with fresh butane feed though supply means (4). Waste gas such as carbon oxides are vented from separation means (18) through line (20).

The reaction conditions expected to be present in the process of the present invention were studied in the following batch autoclave experiments. Although these had a gas/liquid interface with an overhead gas phase, the conditions in the liquid composition were indicative of those expected in the process according to the present invention. Nitrogen was introduced at the beginning of these experiments to dilute the oxygen is the overhead gas phase.

Experiment 1—Typical reaction procedure

A titanium autoclave equipped with a stirrer, thermocouple, cooling coil and gas and butane feed ports and with a nominal internal volume of 300 cm$^3$ was charged with a mixture of: acetic acid (48.3 g), acetone (0.5 g), butan-2-one (3.5 g), butyric acid (5.5 g), propionic acid (4.7 g), sec-butyl acetate (3.9 g), ethyl acetate (2.2 g), methyl acetate (1.2 g), water (7.9 g) and cobalt(II) acetate tetrahydrate (2.3 g). This mixture was selected because the liquid components were believed to be representative of the liquid components that would be present in the second liquid reaction composition withdrawn from the bubble column reaction zone in a continuous butane oxidation process according to the present invention.

The autoclave was sealed and butane (36 g) added. Nitrogen was added to give a pressure of about 80 barg and the temperature then raised to a set temperature of 140° C., giving a total pressure in the range 105–120 barg. Gas from the overhead gas phase was released from the autoclave until the pressure was 104 barg. Oxygen was added from a ballast vessel to give a pressure of 115 barg, and the gas handling system from the ballast vessel was arranged so as to maintain the total pressure in the reactor at not less than 115 barg. After four minutes the reaction initiated and the temperature increased momentarily, before being brought under control by the cooling system. Over the period 2 to 4 minutes after initiation of the reaction, during which the average temperature was 142° C., the rate of uptake of oxygen, measured by linear regression over this period, was 15.9 mol $O_2$/hour.liter of cold reactor charge (taking volume of cold charge as 137.6 cm$^3$). The reaction was allowed to continue until gas uptake ceased, and then the reactor was cooled and the gases vented. Details of the components charged and of the analysis of the liquid products are shown in Table 1.

TABLE 1

|  | Charged (g) | Product Mass (g) | Increase in Mass (g) |
|---|---|---|---|
| Acetone | 0.5 | 0.4 | −0.1 |
| Methyl Acetate | 1.2 | 1.0 | −0.2 |
| Butan-2-one | 3.5 | 2.8 | −0.8 |
| Ethyl Acetate | 2.2 | 1.7 | −0.5 |

TABLE 1-continued

|  | Charged (g) | Product Mass (g) | Increase in Mass (g) |
|---|---|---|---|
| sec-Butyl Acetate | 3.9 | 3.1 | −0.8 |
| Acetic Acid | 48.3 | 62.5 | 14.2 |
| Propionic Acid | 4.7 | 6.1 | 1.4 |
| Butyric Acid | 5.5 | 3.6 | −1.9 |
| Water | 7.9 | 13.1 | 5.2 |

Experiment 2. Effect of partial pressure of oxygen on reaction rate

Figure 2:
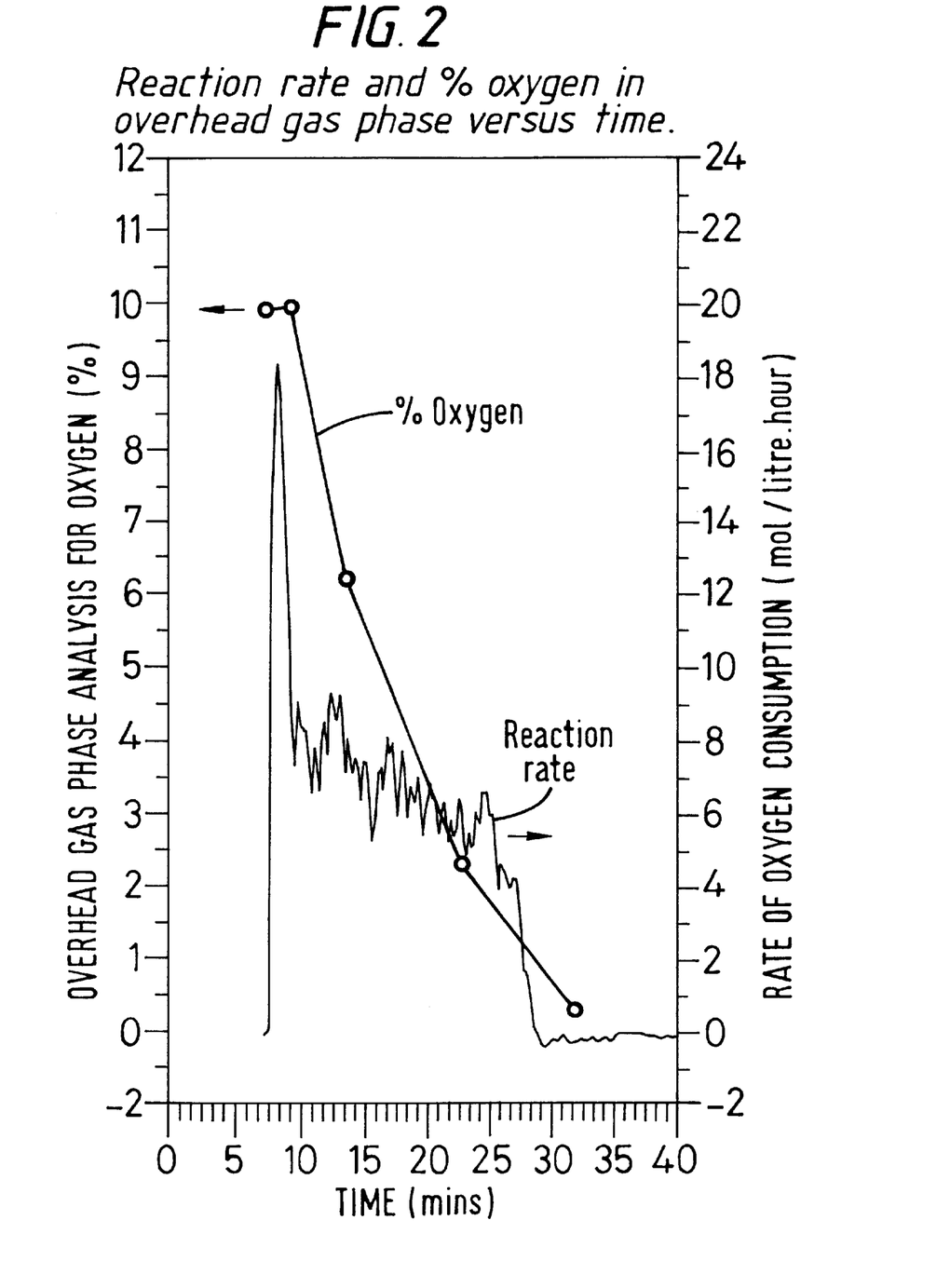
FIG. 2 is a graph of reaction rate and percentage oxygen in the overhead gas phase versus time for batch autoclave experiments for butane oxidation.

The procedure of Experiment 1 was followed in a series of reaction runs except that the amount of catalyst used was 1.13 g and the set temperature was 135° C. The reactions were terminated before the oxygen demand fell to zero by closing the oxygen inlet and immediately sampling the overhead gas phase. A series of reaction runs was done under the same conditions where the runs were terminated at various times after initiation of the reaction. FIG. 2 shows both the reaction rate during the course of one reaction and a corresponding plot of the oxygen concentration of the reactor overhead gas phase when the reaction was terminated with time taken for the series of reaction runs. It can be seen from FIG. 2 that the reaction rate is approximately constant at 6–8 mol $O_2$/liter.hour as the oxygen concentration in the reactor overhead gas phase declines from about 10% to about 2% v/v (11 bar to 2 bar) and then falls rapidly to zero as the oxygen concentration declines to zero. The reaction profile up to termination was very similar in all reaction runs. Two different kinetic regimes were observed. The kinetics at an oxygen vapour concentration of greater than about 2.5% v/v (2.5 bar) represent the kinetics expected to be present in the first reaction zone and the kinetics of the later part of the reaction run were different.

Experiment 3. Addition of oxygen to re-start reactions

Figure 3:
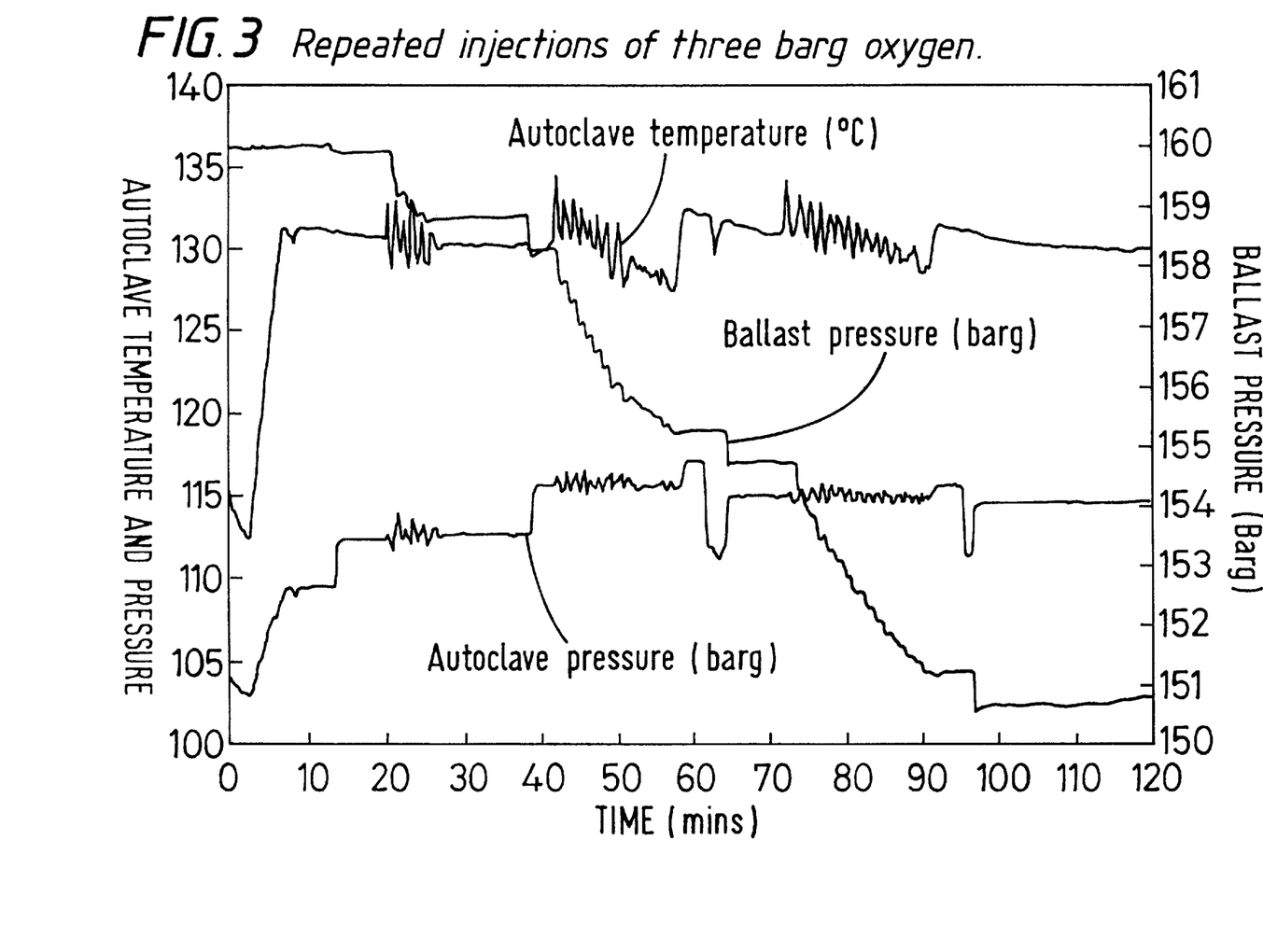
FIG. 3 is a graph of ballast pressure versus time to show the effect of sudden increases in partial pressure of oxygen on reaction rate.

The procedure of Experiment 1 was followed except that only 1.12 g catalyst was used, the set temperature was 130° C. and only three bar of oxygen was added. Following completion of the reaction (at which point the oxygen partial pressure was believed to be zero) a further three bar of oxygen was added to re-initiate the reaction. The profile of ballast pressure with time is shown in FIG. 3. FIG. 3 shows how the addition of extra oxygen to a completed reaction causes the reaction to restart (reaction rate as measured by the consumption of oxygen from a ballast vessel).

Experiment 4. Effect of the partial pressure of oxygen on reaction rate at high partial pressures of oxygen The procedure of Experiment 1 was followed in a series of reactions except that di-tertiary-butyl peroxide (1 g) was added to aid initiation, the amount of catalyst used was 1.13 g, the set temperature was 130° C. and the amount of oxygen added in the initial charge was varied. The reaction rate is calculated in two ways:—(a) by linear regression of the ballast vessel pressure drop rate over the period 2–4 minutes after reaction initiation and (b) from the total ballast vessel pressure drop over the period 1.8 to 4.8 minutes after initiation of the reaction. The results, presented in Table 2, show that, for a given catalyst concentration, high rates of reaction can be obtained over a range of partial pressure of oxygen.

TABLE 2

Effect of Oxygen Partial Pressure on Reaction Rate

| Nominal Temperature | 130 | 130 | 130 | 130 | 130 | 130 |
|---|---|---|---|---|---|---|
| $P(O_2)$ (bar) | 3 | 5 | 7 | 7 | 9 | 11 |
| wt % Cobalt | 0.23 | 0.23 | 0.23 | 0.23 | 0.23 | 0.23 |
| Cobalt Acetate Tetrahydrate (g) | 1.13 | 1.13 | 1.13 | 1.12 | 1.13 | 1.13 |
| Average Temperature over 2–4 minutes following initiation | 131 | 130 | 130 | 130 | 131 | 131 |
| Regressed Rate [mol/l.h] (covers rate 2–4 minutes after initiation, using charge volume = 138.9 cm³) | 6.0 | 5.6 | 5.1 | 4.5 | 6.0 | 8.6 |
| Rate [mol/l.h] based on total pressure drop of ballast vessel over 1.8 to 4.8 minutes after initiation. | 5.8 | 6.8 | 5.4 | 6.9 | 6.3 | 6.7 |

Experiment 5. Effect of catalyst concentration on reaction rate at high partial pressures of oxygen The procedure of Experiment 1 was followed in a series of experiments except that: di-tertiary-butyl peroxide (1 g) was added to aid initiation; the set temperature was 130° C.; the amount of oxygen added was 7 bar and the amount of catalyst was varied. The results are presented in Table 3. They show that, for a given partial pressure of oxygen, the reaction rate is greater at higher catalyst concentration.

TABLE 3

Effect of Catalyst Concentration on Reaction Rate

| Nominal Temperature | 130 | 130 | 130 | 130 | 130 |
|---|---|---|---|---|---|
| $P(O_2)$ (bar) | 7 | 7 | 7 | 7 | 7 |
| wt % Cobalt | 0.019 | 0.083 | 0.23 | 0.23 | 0.68 |
| Cobalt Acetate Tetrahydrate (g) | 0.092 | 0.401 | 1.13 | 1.12 | 3.39 |
| Average Temperature over 2–4 minutes following initiation | 130 | 132 | 130 | 130 | 131 |
| Regressed Rate [mol/l.h] (covers rate 2-4 minutes after initiation, using charge volume = 138.9 cm³) | 1.8 | 4.5 | 5.1 | 4.5 | 9.8 |
| Rate [mol/l.h] based on the total pressure drop of ballast vessel over 1.8 to 4.8 minutes after initiation. | 1.2 | 6.9 | 5.4 | 6.9 | 9.8 |

Experiment 6. Effect of temperature on reaction rate at high partial pressures of oxygen The procedure of Experiment 1 was followed in a series of experiments except that: di-tertiary-butyl peroxide (1 g) was added to aid initiation; the amount of catalyst use was 1.13 g and the temperature of the reactions were varied. The results are presented in Table 4 and show that the reaction rate increases with temperature.

TABLE 4

Effect of Temperature on Reaction Rate

| | | | | |
|---|---|---|---|---|
| Nominal Temperature | 130 | 135 | 140 | 145 |
| P(O$_2$) (bar) | 11 | 11 | 11 | 11 |
| wt % Cobalt | 0.23 | 0.23 | 0.23 | 0.23 |
| Cobalt Acetate Tetrahydrate (g) | 1.13 | 1.13 | 1.13 | 1.13 |
| Average Temperature over 2–4 minutes following initiation | 131 | 137 | 142 | 147 |
| Regressed Rate [mol/l.h] (covers rate 2–4 minutes after initiation, using charge volume = 138.9 cm$^3$) | 8.6 | 9.4 | 10.0 | 14.4 |
| Rate [mol/l.h] based on total pressure drop of ballast vessel over 1.8 to 4.8 minutes after initiation. | 6.7 | 8.0 | 12.2 | 16.0 |

Experiment 7. Effect of oxygen partial pressure at high catalyst concentration

The procedure of Experiment 1 was followed in a pair of experiments except that the amount of catalyst used was 3.4 g, the temperature was 130° C. and the oxygen partial pressure was varied. The experiment with higher partial pressure of oxygen contained 1 g di-tertbutyl peroxide to aid initiation. The results are presented in Table 5 and show that, under the reaction conditions of high catalyst concentration, reaction rate increases with increasing oxygen partial pressure.

TABLE 5

Effect of oxygen partial pressure on reaction rate.

| | | |
|---|---|---|
| Nominal Temperature | 130 | 130 |
| P(O$_2$) (bar) | 7 | 3.2 |
| wt % Cobalt | 0.68 | 0.68 |
| Cobalt Acetate Tetrahydrate (g) | 3.39 | 3.41 |
| Average temperature 2–4 minutes following initiation | 131 | 131 |
| Rate [mol O$_2$/liter.hour] based on total pressure drop of ballast vessel over 2–4 minutes after initiation. | 8.4 | 2.8 |

Experiments 1 to 7 demonstrate that the oxidation of butane with oxygen in the presence of a cobalt catalyst and a solvent at a temperature in the range 130° to 150° C. and at a partial pressure of oxygen of greater than 2 bar gives high reaction rates and good selectivity to acetic acid. These examples are representative, but not limiting, of the conditions present in the first reaction zone of the present invention, except that an overhead gas phase is present in Experiments 1 to 7 as a consequence of the autoclave apparatus employed.

Experiment 8. Effect of the partial pressure of oxygen on reaction rate at low partial pressures of oxygen The procedure of Experiment 1 was followed except that di-tertiary-butyl peroxide (1 g) was added to aid initiation; the amount of oxygen added in the initial charge was only 7 bar; the amount of catalyst added was 3.39 g (3% cobalt acetate tetrahydrate). The results are presented in FIGS. 4a and 4b, from which it can be seen that the reaction rate declines with time, reflecting the declining partial pressure of oxygen.

Figure 4A:
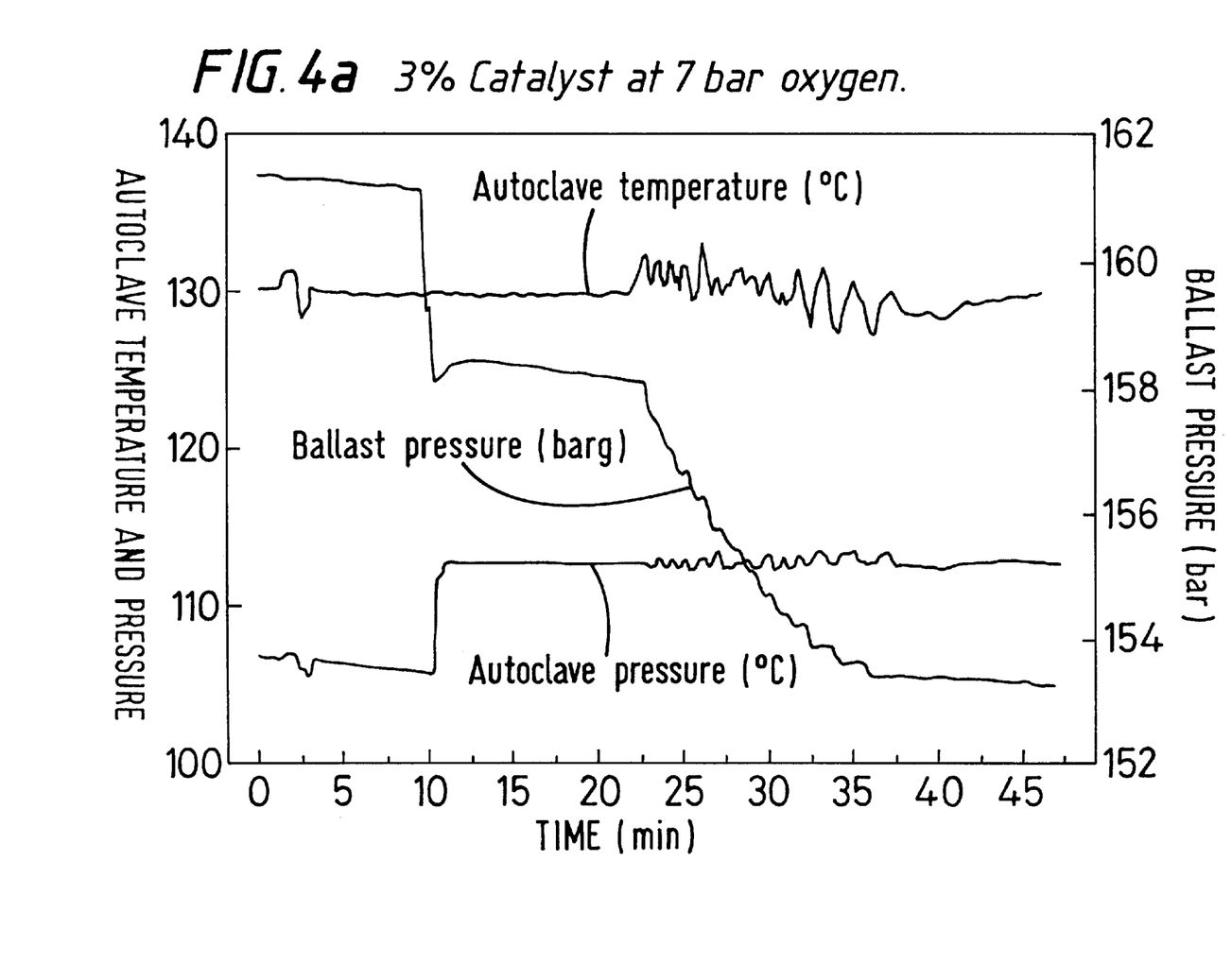
Figure 4B:
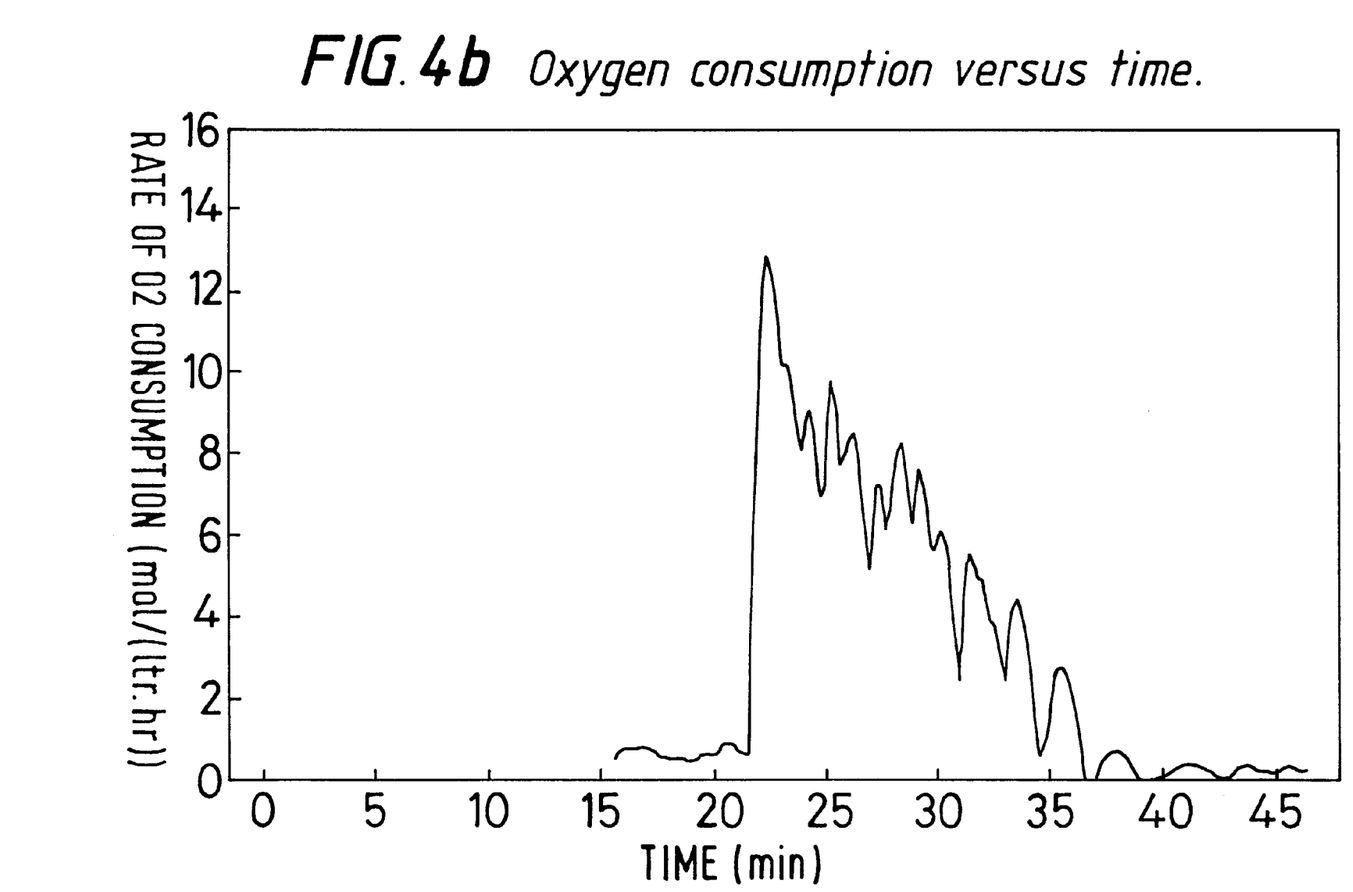

The bubble column reaction zone according to the preferred embodiment of the present invention has oxygen distributed through the reactor so that the notional partial pressure decreases from the bottom to the top. Thus the variation of reaction rate with time in this experiment is analogous to the variation of rate with distance from the base of the bubble column reaction zone, in that, in both cases, the reaction rate reflects the partial pressure of oxygen present.

Figure 5:
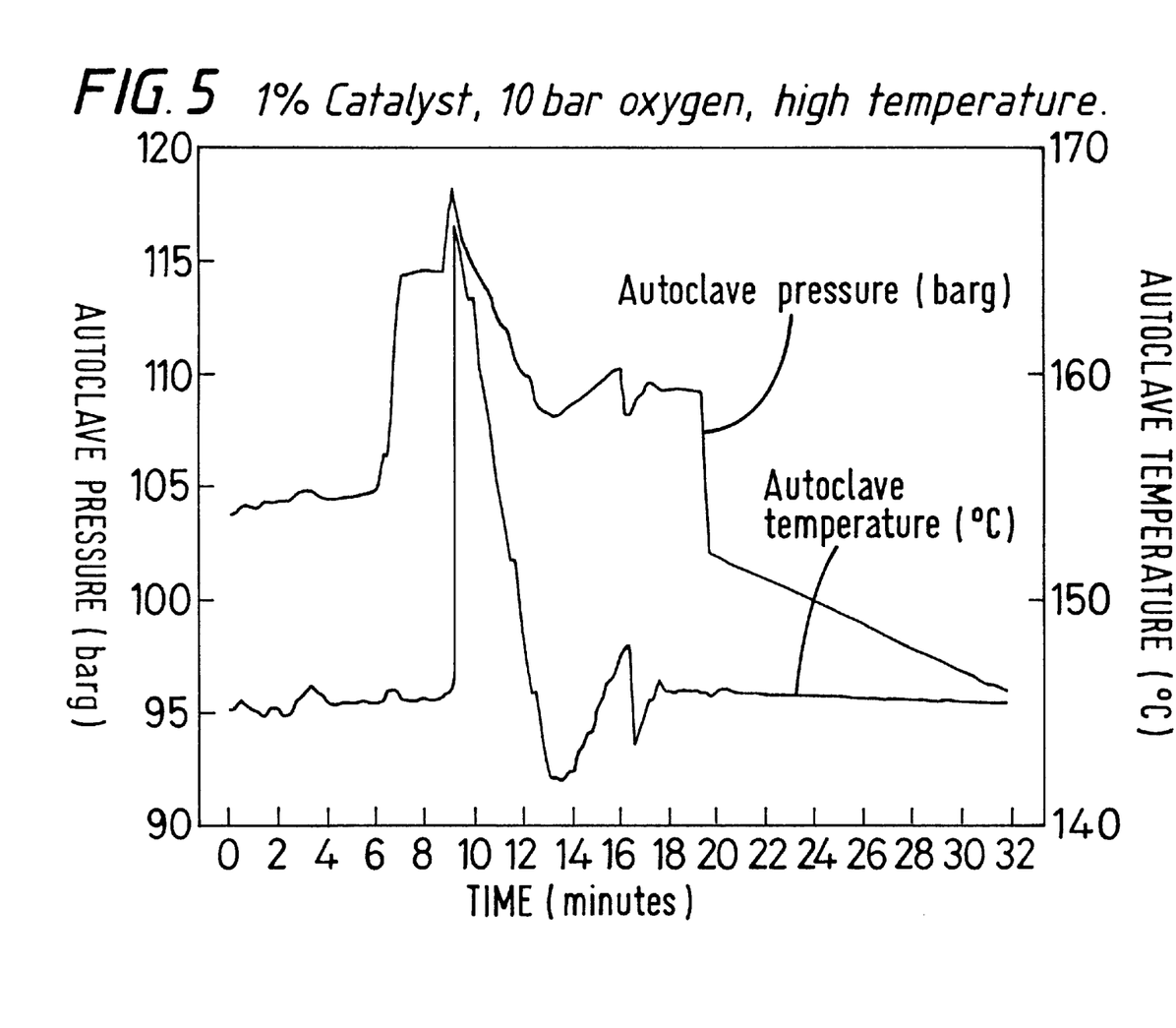
FIG. 5 is a graph of autoclave pressure and temperature versus time.

Experiment 9. Effect of allowing temperature to increase in the absence of supplied oxygen The procedure of Experiment 1 was followed except that the amount of catalyst used was 1.13 g (1 wt. % cobalt acetate tetrahydrate), the set temperature as 145° C. and, after the initial charge of oxygen, the oxygen supply line was closed and the cooling water turned off. The effect on the temperature profile of the reaction is shown in FIG. 5. A sudden exotherm was observed. The extreme nature of this sudden exotherm indicates that the reaction proceeded rapidly to completion in the absence of water cooling. This indicates that in the bubble column reaction zone of the invention, the reaction will proceed to completion using the large heat of the reaction.

Figure 6:
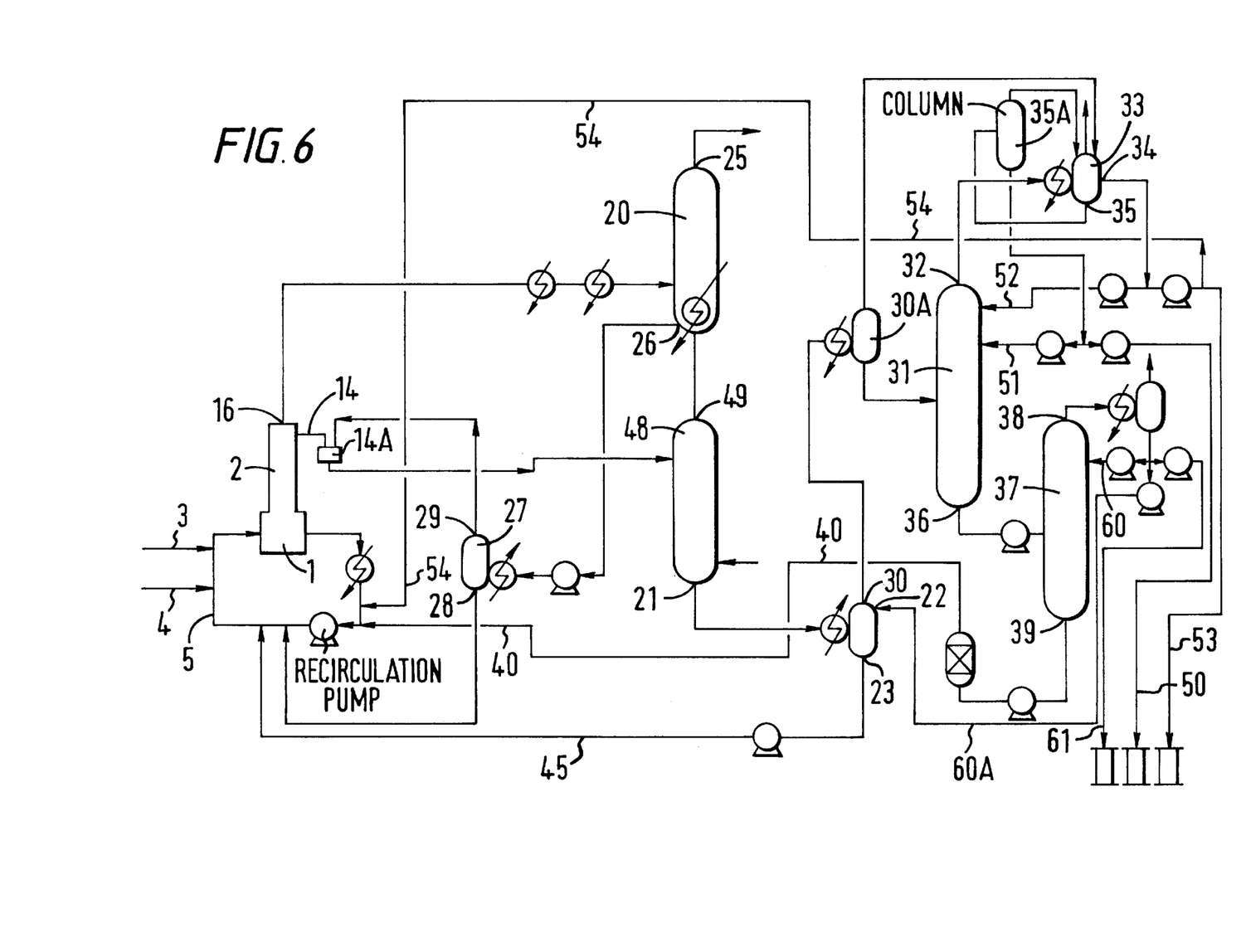
FIG. 6 is a schematic flow diagram for a butane oxidation apparatus according to the present invention.

FIG. 6 is a schematic flow diagram of apparatus for use in a butane oxidation process according to the present invention. In use, liquid reaction composition is withdrawn from near the top of a bubble column reaction zone (2) through outlet (14) and is passed to separation vessel 14A. Liquid from the base of vessel (14A) is passed to a stripper (48) where butane and carbon dioxide are removed from the liquid stream through outlet (49) and are passed to a separator (20). The liquid from the stripper is passed through outlet (21) to a catalyst flash (22) from the base of which (outlet 23) a stream containing catalyst is recycled along line (45) to recycle inlet (5) to the first reaction zone (1). Oxygen and butane feeds to the first reaction zone (1) are added to recycle inlet (5) just prior to its introduction to the reactor through inlets, (3) and (4) respectively. A vapour stream is withdrawn from the overhead gas phase at the top of the bubble column reaction zone through outlet (16) and is passed to the separator (20) where carbon dioxide is partially separated from the butane and other liquids and the carbon dioxide is vented through outlet (25) and thence to an oxygen analyser not shown. The butane and other liquids leave the separator through outlet (26) and are recycled to the reactor via a hot flash (27) which further separates the butane and other liquids from dissolved carbon dioxide. The butane and other liquids exit the hot flash through outlet (28) and are recycled to the first reaction zone via recycle inlet (5) and the carbon dioxide is passed to separation vessel (14A) via outlet (29) and then on to the bubble column reaction zone via line 14.

The vapour phase from the catalyst hot flash (22) exits the catalyst flash through outlet (30) and is cooled and condensed in vessel 30A. The vapour is passed to decanter 33 and the liquid is passed to an acid drying column (31) where lights and water are withdrawn overhead through outlet (32) to a decanter (33) From the decanter, water exits through outlet (35) to column (35A). Vapour from the column is returned to decanter (33). Liquid from the column is part returned to the acid drying column along line (51), and part is discharged along line (50). Organic components may be recovered by distillation (not shown) from the water discharged from the decanter along line (50) and recycled to the decanter. The lights are withdrawn from the decanter through outlet (34), part is returned to the acid drying column by line (52) and part to the reactor (1) along line (54) (also some may be removed along line (53)). The liquid take-off from the base of the acid drying column is passed through outlet (36) to a second column (37) from which acetic acid product is taken overhead through outlet (38) as vapour, part being returned to column (37) as reflux along line (60) part being returned via line (60A) to the head of the catalyst flash vessel (22), and the remainder as product along line (61). The liquid from the base of the column exits through outlet (39) and is returned to the reactor (1) through line (40).

We claim:

1. A process for the liquid phase oxidation of butane to produce acetic acid which comprises reacting oxygen and butane in the presence of a cobalt catalyst in a liquid reaction composition in an oxygen in an oxidation reaction zone at a temperature in the reaction zone in the range 136° to 150° C., whilst continuously maintaining a concentration of oxygen throughout the reaction zone equivalent to a partial pressure of oxygen greater than 2 bar and a concentration of cobalt oxidation catalyst in the liquid reaction composition of at least 0.12% by weight cobalt and up to its limit of solubility in the liquid reaction composition.

2. A process claimed in claim 1 wherein the oxygen concentration is equivalent to a partial pressure of oxygen greater than 4 bar.

3. A process as claimed in claim 1 carried out under a total pressure of 35 barg.

4. A process as claimed in claim 2 carried out under a total pressure of 35 barg.

5. A process for the production of acetic acid which comprises:

(a) reacting oxygen and butane at a temperature in the range 120° to 180° C., in a recirculating first liquid reaction composition in a first reaction zone to produce acetic acid, the first liquid reaction composition comprising cobalt oxidation catalyst, butane, dissolved oxygen, acetic acid and water, and having no gas/liquid interface with an overhead gas phase, whilst continuously maintaining a concentration of oxygen throughout the first reaction zone equivalent to a partial pressure of oxygen greater than 2 bar, and a concentration of cobalt oxidation catalyst in the first liquid reaction composition of at least 0.12% by weight cobalt and up to its limit of solubility in the first liquid reaction composition;

(b) withdrawing from the first reaction zone at least a portion of the first liquid reaction composition, together with entrained oxygen, and passing it to a bubble column reaction zone in which there is maintained a second liquid reaction composition comprising cobalt oxidation catalyst, butane, dissolved oxygen, acetic acid and water, and reacting the entrained and dissolved oxygen with butane in the second liquid reaction composition in the bubble column reaction zone to produce further acetic acid; said second liquid reaction composition being in contact with an overhead gas phase comprising oxygen at a concentration less than the lower flammability limit of the oxygen therein;

(c) withdrawing at least a portion of the second liquid reaction composition from the bubble column reaction zone, recovering acetic acid and optionally other co-products therefrom and recycling to the first reaction zone cobalt oxidation catalyst from the withdrawn composition; and (d) withdrawing overhead gas phase from the bubble column reaction zone, separating unreacted butane reactant therefrom and recycling it to the first reaction zone.

* * * * *